(12) United States Patent
Falana et al.

(10) Patent No.: US 8,362,298 B2
(45) Date of Patent: Jan. 29, 2013

(54) HYDROLYZED NITRILOTRIACETONITRILE COMPOSITIONS, NITRILOTRIACETONITRILE HYDROLYSIS FORMULATIONS AND METHODS FOR MAKING AND USING SAME

(75) Inventors: Olusegun M. Falana, San Antonio, TX (US); Aziz Hikem, San Antonio, TX (US); Sarkis R. Kakadjian, San Antonio, TX (US); Frank Zamora, Edo Merida (VE)

(73) Assignee: Clearwater International, LLC, Houston, TX (US)

( * ) Notice: Subject to any disclaimer, the term of this patent is extended or adjusted under 35 U.S.C. 154(b) by 0 days.

(21) Appl. No.: 13/112,012

(22) Filed: May 20, 2011

(65) Prior Publication Data

US 2011/0218125 A1    Sep. 8, 2011

Related U.S. Application Data

(62) Division of application No. 12/176,872, filed on Jul. 21, 2008, now Pat. No. 7,956,217.

(51) Int. Cl.
C07C 55/22    (2006.01)
(52) U.S. Cl. .................................................... 562/590
(58) Field of Classification Search ........................ None
See application file for complete search history.

(56) References Cited

U.S. PATENT DOCUMENTS

| | | | |
|---|---|---|---|
| 2,196,042 A | 4/1940 | Timpson | 23/11 |
| 2,390,153 A | 12/1945 | Kern | 260/72 |
| 2,805,958 A | 7/1959 | Bueche et al. | 106/308 |
| 3,059,909 A | 10/1962 | Wise | 261/39.3 |
| 3,163,219 A | 12/1964 | Wyant et al. | 166/283 |
| 3,301,723 A | 1/1967 | Chrisp | 149/20 |
| 3,301,848 A | 1/1967 | Halleck | 536/123.1 |
| 3,303,896 A | 2/1967 | Tillotson et al. | 175/69 |
| 3,317,430 A | 5/1967 | Priestley et al. | 510/503 |
| 3,393,234 A * | 7/1968 | Wollensak | 562/554 |
| 3,565,176 A | 2/1971 | Wittenwyler | 166/270 |
| 3,856,921 A | 12/1974 | Shrier et al. | 423/228 |
| 3,888,312 A | 6/1975 | Tiner et al. | 166/308.5 |
| 3,933,205 A | 1/1976 | Kiel | 166/308.1 |
| 3,937,283 A | 2/1976 | Blauer et al. | 166/307 |
| 3,960,736 A | 6/1976 | Free et al. | 507/216 |
| 3,965,982 A | 6/1976 | Medlin | 166/249 |
| 3,990,978 A | 11/1976 | Hill | 507/235 |
| 4,007,792 A | 2/1977 | Meister | 166/308.2 |
| 4,052,159 A | 10/1977 | Fuerst et al. | |
| 4,067,389 A | 1/1978 | Savins | 166/246 |
| 4,108,782 A | 8/1978 | Thompon | 507/205 |
| 4,112,050 A | 9/1978 | Sartori et al. | 423/223 |
| 4,112,051 A | 9/1978 | Sartori et al. | 423/223 |
| 4,112,052 A | 9/1978 | Sartori et al. | 423/223 |
| 4,113,631 A | 9/1978 | Thompson | 507/202 |
| 4,378,845 A | 4/1983 | Medlin et al. | 166/297 |
| 4,461,716 A | 7/1984 | Barbarin et al. | 252/307 |
| 4,479,041 A | 10/1984 | Fenwick et al. | 200/81 R |
| 4,506,734 A | 3/1985 | Nolte | 166/308.1 |
| 4,514,309 A | 4/1985 | Wadhwa | 507/211 |
| 4,541,935 A | 9/1985 | Constien et al. | 507/225 |
| 4,549,608 A | 10/1985 | Stowe et al. | 166/280.1 |
| 4,561,985 A | 12/1985 | Glass, Jr. | 507/108 |
| 4,623,021 A | 11/1986 | Stowe | 166/250.1 |
| 4,654,266 A | 3/1987 | Kachnik | 428/403 |
| 4,657,081 A | 4/1987 | Hodge | 166/380.5 |
| 4,660,643 A | 4/1987 | Perkins | 166/283 |
| 4,683,068 A | 7/1987 | Kucera | 507/201 |
| 4,686,052 A | 8/1987 | Baranet et al. | 507/244 |
| 4,695,389 A | 9/1987 | Kubala | 507/244 |
| 4,705,113 A | 11/1987 | Perkins | 166/302 |
| 4,714,115 A | 12/1987 | Uhri | 166/308.1 |
| 4,718,490 A | 1/1988 | Uhri | 166/281 |
| 4,724,905 A | 2/1988 | Uhri | 166/250.1 |
| 4,725,372 A | 2/1988 | Teot et al. | 507/129 |
| 4,739,834 A | 4/1988 | Peiffer et al. | 166/308.4 |
| 4,741,401 A | 5/1988 | Walles et al. | 166/300 |
| 4,748,011 A | 5/1988 | Baize | 423/228 |
| 4,779,680 A | 10/1988 | Sydansk | 166/300 |
| 4,795,574 A | 1/1989 | Syrinek et al. | 507/238 |
| 4,817,717 A | 4/1989 | Jennings, Jr. et al. | 166/278 |
| 4,830,106 A | 5/1989 | Uhri | 166/250.1 |
| 4,846,277 A | 7/1989 | Khalil et al. | 166/280.1 |
| 4,848,468 A | 7/1989 | Hazlett et al. | 166/300 |
| 4,852,650 A | 8/1989 | Jennings, Jr. et al. | 166/250.1 |
| 4,869,322 A | 9/1989 | Vogt, Jr. et al. | 166/280.1 |
| 4,892,147 A | 1/1990 | Jennings, Jr. et al. | 166/280.2 |
| 4,926,940 A | 5/1990 | Stromswold | 166/247 |
| 4,938,286 A | 7/1990 | Jennings, Jr. | 166/280.1 |
| 4,978,512 A | 12/1990 | Dillon | 423/226 |
| 5,005,645 A | 4/1991 | Jennings, Jr. et al. | 166/280.1 |
| 5,024,276 A | 6/1991 | Borchardt | 166/308.6 |
| 5,067,556 A | 11/1991 | Fudono et al. | 62/196.4 |
| 5,074,359 A | 12/1991 | Schmidt | 166/280.1 |

(Continued)

OTHER PUBLICATIONS

U.S. Appl. No. 13/117,304, filed May 27, 2011, Falana et al.

(Continued)

*Primary Examiner* — Paul A Zucker
(74) *Attorney, Agent, or Firm* — Robert W Strozier

(57) ABSTRACT

Hydrolyzed nitrilotriacetonitrile compositions are disclosed prepared by a method characterized by a one-shot addition of an amount of nitrilotriacetonitrile to a solution containing an acid catalyst, where the reaction is complete in a time period of less than an hour. The method is also characterized by adjusting the pH of the reaction mixture to a pH of at least 8. The method is also characterized by oxidatively removing free cyanide to a desired low level through the addition of an oxidizing agent the produces environmentally benign by-products to the crude hydrolyzed NTAN to form hydrolyzed NTAN compositions having minimized, negligible, or substantially no free cyanide levels.

10 Claims, 7 Drawing Sheets

U.S. PATENT DOCUMENTS

| | | | |
|---|---|---|---|
| 5,074,991 A | 12/1991 | Weers | 208/236 |
| 5,082,579 A | 1/1992 | Dawson | 507/211 |
| 5,106,518 A | 4/1992 | Cooney et al. | 507/21 |
| 5,110,486 A | 5/1992 | Manalastas et al. | 507/260 |
| 5,169,411 A | 12/1992 | Weers | 44/421 |
| 5,224,546 A | 7/1993 | Smith et al. | 166/300 |
| 5,228,510 A | 7/1993 | Jennings, Jr. et al. | 166/263 |
| 5,246,073 A | 9/1993 | Sandiford et al. | 166/295 |
| 5,259,455 A | 11/1993 | Nimerick et al. | 166/308.5 |
| 5,330,005 A | 7/1994 | Card et al. | 166/280.2 |
| 5,342,530 A | 8/1994 | Aften et al. | 252/8.551 |
| 5,347,004 A | 9/1994 | Rivers et al. | 544/180 |
| 5,363,919 A | 11/1994 | Jennings, Jr. | 166/308.1 |
| 5,402,846 A | 4/1995 | Jennings, Jr. et al. | 166/259 |
| 5,411,091 A | 5/1995 | Jennings, Jr. | 166/280.1 |
| 5,424,284 A | 6/1995 | Patel et al. | 507/129 |
| 5,439,055 A | 8/1995 | Card et al. | 166/280.2 |
| 5,462,721 A | 10/1995 | Pounds et al. | 423/226 |
| 5,465,792 A | 11/1995 | Dawson et al. | 166/295 |
| 5,472,049 A | 12/1995 | Chaffe et al. | 166/250.1 |
| 5,482,116 A | 1/1996 | El-Rabaa et al. | 166/250.1 |
| 5,488,083 A | 1/1996 | Kinsey, III et al. | 507/211 |
| 5,497,831 A | 3/1996 | Hainey et al. | 166/308.1 |
| 5,501,275 A | 3/1996 | Card et al. | 166/280.2 |
| 5,551,516 A | 9/1996 | Norman et al. | 166/308.2 |
| 5,624,886 A | 4/1997 | Dawson et al. | 507/217 |
| 5,635,458 A | 6/1997 | Lee et al. | 507/240 |
| 5,649,596 A | 7/1997 | Jones et al. | 166/300 |
| 5,669,447 A | 9/1997 | Walker et al. | 166/300 |
| 5,674,377 A | 10/1997 | Sullivan, III et al. | 208/208 R |
| 5,688,478 A | 11/1997 | Pounds et al. | 423/226 |
| 5,693,837 A | 12/1997 | Smith et al. | 556/148 |
| 5,711,396 A | 1/1998 | Joerg et al. | 180/444 |
| 5,722,490 A | 3/1998 | Ebinger | 166/281 |
| 5,744,024 A | 4/1998 | Sullivan, III et al. | 208/236 |
| 5,755,286 A | 5/1998 | Ebinger | 166/281 |
| 5,775,425 A | 7/1998 | Weaver et al. | 166/276 |
| 5,787,986 A | 8/1998 | Weaver et al. | 166/280.2 |
| 5,806,597 A | 9/1998 | Tjon-Joe-Pin et al. | 166/300 |
| 5,807,812 A | 9/1998 | Smith et al. | 507/238 |
| 5,833,000 A | 11/1998 | Weaver et al. | 166/276 |
| 5,853,048 A | 12/1998 | Weaver et al. | 166/279 |
| 5,871,049 A | 2/1999 | Weaver et al. | 166/276 |
| 5,877,127 A | 3/1999 | Card et al. | 507/273 |
| 5,908,073 A | 6/1999 | Nguyen et al. | 166/276 |
| 5,908,814 A | 6/1999 | Patel et al. | 507/131 |
| 5,964,295 A | 10/1999 | Brown et al. | 166/308.2 |
| 5,979,557 A | 11/1999 | Card et al. | 166/300 |
| 5,980,845 A | 11/1999 | Cherry | 423/229 |
| 6,016,871 A | 1/2000 | Burts, Jr. | 166/300 |
| 6,035,936 A | 3/2000 | Whalen | 166/308.5 |
| 6,047,772 A | 4/2000 | Weaver et al. | 166/276 |
| 6,054,417 A | 4/2000 | Graham et al. | 507/238 |
| 6,059,034 A | 5/2000 | Rickards et al. | 166/280.2 |
| 6,060,436 A | 5/2000 | Snyder et al. | 507/266 |
| 6,069,118 A | 5/2000 | Hinkel et al. | 507/277 |
| 6,123,394 A | 9/2000 | Jeffrey | 299/16 |
| 6,133,205 A | 10/2000 | Jones | 507/276 |
| 6,147,034 A | 11/2000 | Jones et al. | 507/238 |
| 6,162,449 A | 12/2000 | Maier et al. | 424/401 |
| 6,162,766 A | 12/2000 | Muir et al. | 507/267 |
| 6,169,058 B1 | 1/2001 | Le et al. | 507/222 |
| 6,228,812 B1 | 5/2001 | Dawson et al. | 507/221 |
| 6,247,543 B1 | 6/2001 | Patel et al. | 175/64 |
| 6,267,938 B1 | 7/2001 | Warrender et al. | 423/226 |
| 6,283,212 B1 | 9/2001 | Hinkel et al. | 166/279 |
| 6,291,405 B1 | 9/2001 | Lee et al. | 507/136 |
| 6,330,916 B1 | 12/2001 | Rickards et al. | 166/280.2 |
| 6,725,931 B2 | 4/2004 | Nguyen et al. | 166/280.2 |
| 6,756,345 B2 | 6/2004 | Pakulski et al. | 507/246 |
| 6,793,018 B2 | 9/2004 | Dawson et al. | 166/300 |
| 6,832,650 B2 | 12/2004 | Nguyen et al. | 166/279 |
| 6,875,728 B2 | 4/2005 | Gupta et al. | 507/240 |
| 7,140,433 B2 | 11/2006 | Gatlin et al. | 166/250.1 |
| 7,268,100 B2 | 9/2007 | Kippie et al. | 507/244 |
| 7,350,579 B2 | 4/2008 | Gatlin et al. | 166/308.3 |
| 7,392,847 B2 | 7/2008 | Gatlin et al. | 166/280.2 |
| 7,517,447 B2 | 4/2009 | Gatlin | 208/236 |
| 7,565,933 B2 | 7/2009 | Kippie et al. | 166/372 |
| 7,566,686 B2 | 7/2009 | Kippie et al. | 507/213 |
| 7,712,535 B2 | 5/2010 | Venditto et al. | 166/308.2 |
| 7,767,628 B2 | 8/2010 | Kippie et al. | 507/102 |
| 7,829,510 B2 | 11/2010 | Gatlin et al. | 507/277 |
| 7,886,824 B2 | 2/2011 | Kakadjian et al. | 166/308.2 |
| 7,915,203 B2 | 3/2011 | Falana et al. | 507/136 |
| 7,932,214 B2 | 4/2011 | Zamora et al. | 507/202 |
| 7,942,201 B2 | 5/2011 | Ekstrand et al. | 133/246 |
| 7,956,017 B2 | 6/2011 | Gatlin et al. | 166/280.2 |
| 7,956,217 B2 | 6/2011 | Falana et al. | 562/572 |
| 7,971,659 B2 | 7/2011 | Gatlin et al. | 510/492 |
| 7,989,404 B2 | 8/2011 | Kakadjian et al. | 507/261 |
| 7,992,653 B2 | 8/2011 | Zamora et al. | 175/65 |
| 8,011,431 B2 | 9/2011 | van Petegen | 166/270 |
| 8,012,913 B2 | 9/2011 | Gatlin et al. | 507/239 |
| 8,028,755 B2 | 10/2011 | Darnell et al. | 166/379 |
| 8,034,750 B2 | 10/2011 | Thompson et al. | 507/273 |
| 8,065,905 B2 | 11/2011 | Sweeney et al. | 73/49.1 |
| 8,084,401 B2 | 12/2011 | Lukocs et al. | 507/238 |
| 8,093,431 B2 | 1/2012 | Falana et al. | 564/471 |
| 8,097,567 B2 | 1/2012 | Wilson, Jr. | 507/131 |
| 8,099,997 B2 | 1/2012 | Curr et al. | 73/49.5 |
| 8,141,661 B2 | 3/2012 | Kakadjian et al. | 175/69 |
| 8,158,562 B2 | 4/2012 | Wilson, Jr. et al. | 507/203 |
| 8,172,952 B2 | 5/2012 | Wanner et al. | 134/22.11 |
| 2002/0049256 A1 | 4/2002 | Bergeron, Jr. | 514/674 |
| 2002/0165308 A1 | 11/2002 | Kinniard et al. | 524/492 |
| 2003/0220204 A1 | 11/2003 | Baran, Jr. et al. | 507/200 |
| 2005/0045330 A1 | 3/2005 | Nguyen et al. | 166/281 |
| 2005/0092489 A1 | 5/2005 | Welton et al. | 166/280.2 |
| 2005/0137114 A1 | 6/2005 | Gatlin et al. | 510/424 |
| 2006/0194700 A1 | 8/2006 | Gatlin et al. | 507/203 |
| 2008/0251252 A1 | 10/2008 | Schwartz | 507/238 |
| 2008/0318812 A1 | 12/2008 | Kakadjian et al. | 507/219 |
| 2009/0250659 A1 | 10/2009 | Gatlin | 208/236 |
| 2009/0275488 A1 | 11/2009 | Zamora et al. | 507/236 |
| 2010/0077938 A1 | 4/2010 | Zamora et al. | 106/677 |
| 2010/0212905 A1 | 8/2010 | van Petegen | 507/236 |
| 2010/0252262 A1 | 10/2010 | Ekstrand et al. | 166/305.1 |
| 2010/0292108 A1 | 11/2010 | Kakadjian | 507/229 |
| 2010/0305010 A1 | 12/2010 | Falana et al. | 507/274 |
| 2010/0311620 A1 | 12/2010 | Kakadjian et al. | 507/266 |
| 2011/0001083 A1 | 1/2011 | Falana et al. | 252/178 |
| 2011/0005756 A1 | 1/2011 | van Petegen | 507/236 |
| 2011/0240131 A1 | 10/2011 | Parker | 137/13 |
| 2011/0247821 A1 | 10/2011 | Thompson et al. | 507/267 |
| 2011/0284247 A1 | 11/2011 | Zamora et al. | 166/295 |
| 2011/0284248 A1 | 11/2011 | Zamora et al. | 166/295 |
| 2012/0071366 A1 | 3/2012 | Falana et al. | 507/202 |
| 2012/0071367 A1 | 3/2012 | Falana et al. | 507/203 |
| 2012/0071370 A1 | 3/2012 | Falana et al. | 507/233 |
| 2012/0073813 A1 | 3/2012 | Zamora et al. | 166/285 |
| 2012/0137752 A1 | 6/2012 | Morrow | 73/49.5 |

OTHER PUBLICATIONS

U.S. Appl. No. 13/247,985, filed Sep. 28, 2011, Veldman et al.
U.S. Appl. No. 13/109,712, filed May 17, 2011, Falana et al.
U.S. Appl. No. 13/102,053, filed May 6, 2011, Falana et al.
U.S. Appl. No. 13/094,806, filed Apr. 26, 2011, Zamora et al.
U.S. Appl. No. 13/052,947, filed Mar. 21, 2011, Kakadjian et al.
U.S. Appl. No. 13/102,053, filed May 6, 2011, Kakadjian et al.
U.S. Appl. No. 13/348,267, filed Jan. 11, 2012, Kakadjian et al.
U.S. Appl. No. 13/249,819, filed Sep. 30, 2011, Falana et al.
U.S. Appl. No. 13/348,279, filed Jan. 11, 2012, Falana et al.

* cited by examiner

Cubic crystals of sample WFT 9725-11A formed in the bottom of the test tube (pH = 4.75)

Solution of WFT 9725-11A upon treatment with NH$_4$OH and stirring for 30s (pH = 9.45)

Color Variations in Different Lots of Hydrolyzed NTAN

HYDROLYZED NITRILOTRIACETONITRILE COMPOSITIONS, NITRILOTRIACETONITRILE HYDROLYSIS FORMULATIONS AND METHODS FOR MAKING AND USING SAME

RELATED APPLICATIONS

This application is a divisional of U.S. patent application Ser. No. 12/176,872 filed 21 Jul. 2008 (Jul. 21, 2008) and published as United States Published Application No. 20100012901 published on 21 Jan. 2010 (Jan. 21, 2010), now U.S. Pat. No. 7,956,217 issued 7 Jun. 2011.

BACKGROUND OF THE INVENTION

1. Field of the Invention

The present invention relates to hydrolyzed nitrilotriacetonitrile compositions, nitrilotriacetonitrile hydrolysis methods for preparing the hydrolyzed nitrilotriacetonitrile compositions, and methods for using same.

More particularly, the present invention relates to hydrolyzed nitrilotriacetonitrile compositions, where the method provides an efficient and reproducible nitrilotriacetonitrile hydrolysis method or process for preparing the hydrolyzed nitrilotriacetonitrile compositions, and methods for using same, where the hydrolyzed nitrilotriacetonitrile compositions are substantially cyanide free.

2. Description of the Related Art

Historically, hydrolyzed nitrilotriacetonitrile compositions were obtained by hydrolyzing products over a period of time generally in excess of 3 hour in the presence of an acid as disclosed in U.S. Pat. No. 3,987,077 to Bragdon et. al. followed by boiling the reaction mixture including triacetonitrile in an aqueous metal hydroxide solution. In U.S. Pat. No. 4,547,589 to Shen, Shen prepared nitrilotriacetonitrile compositions in the presence of formaldehyde to remove free cyanide.

Generally, hydrolyzed products are characterized with inconsistencies in hue and composition. Examples of different lot samples are depicted in FIG. 3C. Besides the inconsistencies in composition and color, insoluble crystals mire integrity of hydrolyzed products where solutions of such products are desirable. Consequently, product performance and shelf life are often sacrificed. Additionally, free cyanide ubiquitously associates with nitriloacetonitrile and its resultant hydrolysis products. Free cyanide is highly toxic to both human and the ecosystem. As such, there is need to eliminate it completely or to non-toxic levels and produce hydrolyzed products that meet environmental regulations.

Although several methods for preparing hydrolyzed nitrilotriacetonitrile compositions and the resulting hydrolyzed nitrilotriacetonitrile compositions have been disclosed, there is a need in the art for a more efficient and effective synthetic approach to preparing hydrolyzed nitrilotriacetonitrile compositions, where the compositions have a desired low level cyanide concentration.

SUMMARY OF THE INVENTION

The present invention provides a hydrolyzed nitrilotriacetonitrile (NTAN) composition prepared using a one-shot NTAN addition to a solution containing an acid catalyst, which is pH adjusted after the hydrolysis and treated with an oxidizing agent to reduce, minimize, eliminate, and/or destroy residual free cyanide to a desired low level (low concentration) and in certain embodiments, to a concentration below a free cyanide detection limit.

The present invention provides a method for preparing hydrolyzed NTAN compositions having a desired low concentration of free cyanide, where an amount of NTAN is hydrolyzed in the presence of an acid catalyst for a period of time, generally less than about 40 minutes. The pH of the reaction mixtures is then adjusted to a pH of about 8. After pH adjustment is complete, the composition is treated with an oxidizing agent to reduce, minimize, eliminate or destroy free cyanide to produce a hydrolyzed NTAN composition having a desired low free cyanide concentration. In certain embodiments, the composition is substantially free of cyanide. The method is characterized in that the NTAN addition to the acid solution (or vice versa) over a very short period of time. In certain embodiments, the NTAN is added in a one-shot addition to the acid solution; a single, rapid addition of the NTAN to the acid solution.

BRIEF DESCRIPTION OF THE DRAWINGS

The invention can be better understood with reference to the following detailed description together with the appended illustrative drawings in which like elements are numbered the same.

DEFINITIONS OF TERMS USED IN THE INVENTION

Figure 1:
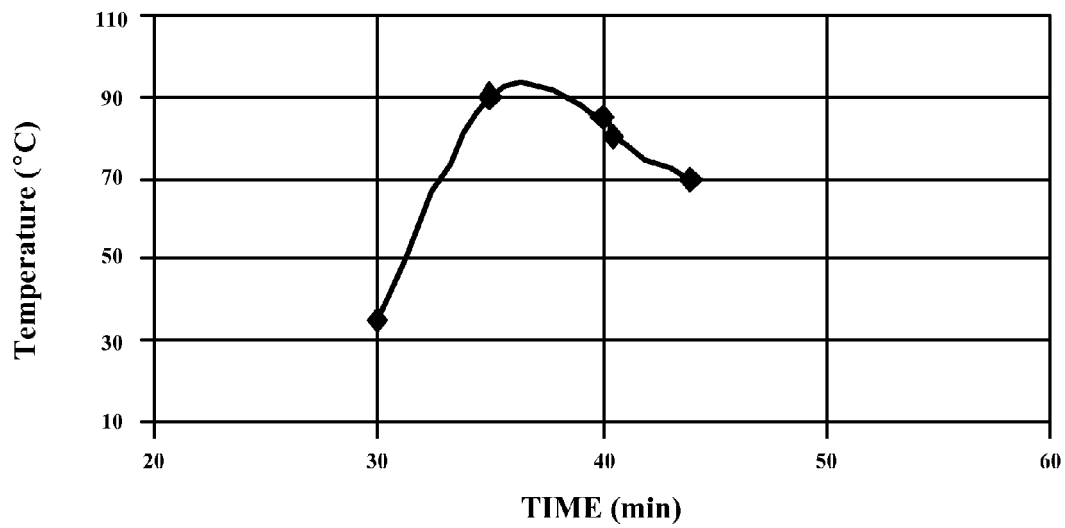
FIG. 1 depicts a NTAN hydrolysis profile of one-shot addition to HCl.

The following definitions are provided in order to aid those skilled in the art in understanding the detailed description of the present invention.

The term "substantially" means that the actual value is within about 5% of the actual desired value, particularly within about 2% of the actual desired value and especially within about 1% of the actual desired value of any variable, element or limit set forth herein.

The term "gpt" means gallons per thousand gallons.

The term "ppt" means pounds per thousand gallons.

The term "FTIR" means Fourier Transformed InfraRed Spectroscopy.

The term "NTAN" means nitrilotriacetonitrile.

The term "substantially cyanide free" or similar terms means that the concentration of free cyanide is no more than 10 ppm ($\leq$10 ppm). In certain embodiments, the terms means that the concentration of free cyanide is no more than 5 ppm ($\leq$5 ppm). In other embodiments, the terms means that the concentration of free cyanide is no more than 1 ppm ($\leq$1 ppm). In other embodiments, the terms means that the concentration of free cyanide is below a free cyanide detection limit.

DETAILED DESCRIPTION OF THE INVENTION

The inventors have found that a new faster, more efficient and effective hydrolytic method for preparing a hydrolyzed nitrilotriacetonitrile (NTAN) composition can be realized, which forms hydrolyzed NTAN compositions having desired low free cyanide concentrations. In certain embodiments, the method forms a substantially cyanide free, hydrolyzed NTAN composition. The new method is characterized by at least the following unique features: (1) a single, rapid or one-shot addition of NTAN to a solution containing an acid catalyst, i.e., the entire NTAN addition to the acid solution occurs over a short or very short period of time; (2) a short reaction time due to the one-shot NTAN addition or a one-shot addition of the acid solution to NTAN; (3) pH adjustment of the reaction mixture after hydrolysis; (4) no external heating; and (5) an addition of an effective amount of an oxidizing agent to the crude hydrolyzed NTAN composition to reduce, minimize or eliminate free cyanide to a desired low level to form the hydrolyzed NTAN compositions having desired low cyanide levels including composition that are substantially cyanide free. Unlike the teaching of Shen (where formaldehyde was explored), the reduction of free cyanide using the oxidizing agents of this invention is environmentally benign.

The inventors have also found that the present process of making hydrolyzed NTAN compositions permits a significantly and surprisingly shorter manufacturing cycle. The short manufacturing cycle is effectuated by controlling a reaction temperature of a one-shot, one-pot hydrolysis reaction, followed by pH adjustment and by adding an effective amount of an oxidizing agent to reduce, minimize or eliminate free cyanide to a desired low level in an environmentally benign cyanide destruction step.

In this invention, NTAN hydrolyzed products were prepared in a period of time under about 40 minutes after a one-time addition—one shot addition—of a desired amount of nitrilotriacetonitrile (NTAN) to a solution containing an acid catalyst such as HCl or other similar mineral or organic acids. Due to the rapid addition, one-shot addition, of NTAN to the acid solution, the reaction is sufficiently exothermic so that no external heating is required. As the reaction subsides (usually marked by drop in reaction temperature), the reaction mixture is brought to a pH of about 8 for optimal destruction free cyanide in the product mixture. Once the pH has been adjusted and optionally at the end of the reaction time period, the reaction mixture is treated with an oxidizing agent to produce a hydrolyzed NTAN composition having a desired low free cyanide concentration and in certain embodiments to produce a substantially cyanide free, hydrolyzed NTAN composition.

Longstanding issues with commercially available hydrolyzed NTAN products such as WFT-9725, a hydrolyzed NTAN crystal forming product having a prohibitively high cyanide levels available from Clearwater International, LLC of Elmendorf, Tex., are solvable using the new process for hydrolyzing NTAN of this invention. Unlike in prior teachings, hydrolyzed NTAN compositions were successfully and reproducibly prepared using the methods described in this invention and compared to prior teaching. For the resulting hydrolyzed NTAN compositions, cyanide was removed to undetectable levels or desired low levels either via heating or by the addition of an oxidizing agent that destroys cyanide producing environmentally benign by-products. Crystallization of the products was found to be dependent on concentration of solids and pH. Products having a very low pH are more likely to form crystals or precipitates than products having a pH close to neutral or higher at various temperatures because of free acid components of the product. Similarly, solids are formed when the water content of the products is low. The former can be resolved by adjusting the pH to form a more soluble product, while the latter can be resolved by adding enough water to solubilize any crystals in the product.

The present novel short duration NTAN hydrolytic methods of this invention include a cyanide destruction step to produce hydrolyzed NTAN compositions having desired low free cyanide concentrations including substantially cyanide free hydrolyzed NTAN compositions. Not only will the reduction in reaction time reduce or minimize labor and energy costs resulting in a more efficient manufacturing process, but the removal of cyanide is of great import to satisfy stringent environmental regulations. A method including a combination of a one shot NTAN addition, a short reaction time, pH adjustment, and an oxidative reduction of cyanide is novel for preparing hydrolyzed NTAN compositions having a reduced or minimized free cyanide level including hydrolyzed NTAN compositions having substantially no free cyanide.

Introduction

Hydrolyzed NTAN compositions are liquid formulations of amide-acids used to inhibit the precipitation of sodium chloride from dehydrated high chloride brines, as metal complexants, prevent caking and flowability of salts. For instance, in Oilfield applications, the compositions are known to eliminate salt build up on tubular configurations and equipment, meter runs and chokes. However, these compositions often have unacceptably high levels of cyanide. To this end, development of a new NTAN hydrolysis method was explored to producing hydrolyzed NTAN compositions having negligible free cyanide levels including composition substantially free of cyanide in a more efficient and effective manner.

Conclusions

A new faster and more efficient NTAN hydrolysis method has been developed. The method is a one-pot, one-shot synthetic procedure, where NTAN is hydrolyzed in the presence of an acid catalyst without external heating. The one-shot addition of NTAN results in a more efficient hydrolysis of NTAN due to the exothermic nature of the reaction. The reaction is then treated with an oxidizing agent adapted to reduce, minimize, remove or destroy free cyanide to a desired low level to generate hydrolyzed NTAN composition having desired low levels of free cyanide including substantially cyanide free compositions. In certain embodiments, the desired low level is a level below a detection limit of free cyanide.

The addition of NTAN in one shot yields a reaction temperature at or below about 90° C. ($\leq$194° F.) guaranteeing a more efficient and cost effective process for manufacturing hydrolyzed NTAN compositions having a reduced or minimized free cyanide concentration including substantially cyanide free hydrolyzed NTAN compositions.

If any crystallization occurs in a product, the crystals can be readily dissolved by increasing pH or addition of ammonium hydroxide and/or water with stirring. Alternatively, an existing winterized formulation can be prepared through the addition of an appropriate wintering agent.

Product color changes are due to $\pi$ to $\pi^*$ transitions that occur in the UV-visible region in carboxylate, cyanide, amide, and/or amino-acid group of the product components.

Suitable acid catalysts includes, without limitation, mineral acids such as HCl, HBr, sulfuric acid, nitric acid, phosphoric acid, or the like, organic acids such as formic acid, acetic acid, trifluoroacetic acid, trichloroacetic acid, triflic acid, or the like, or mixtures or combinations thereof.

Suitable oxidizing agents include, without limitations, alkali hypochlorites such as lithium hypochlorite (LiOCl), sodium hypochlorite (NaOCl), potassium hypochlorite (KOCl), cesium hypochlorite (CsOCl) and rubidium hypochlorite (RbOCl); alkali chlorites such as lithium chlorite ($LiClO_2$), sodium chlorite ($NaClO_2$), potassium chlorite ($KClO_2$), cesium chlorite ($CsClO_2$) and rubidium chlorite ($RbClO_2$), alkaline metal hypochlorites, alkaline metal chlorites, alkali bisulfites, alkaline bisulfites, ammonium bisulfate, sulfur dioxide, sulfur trioxide, chlorine, bromine, other similar oxidizing agents, and mixtures or combinations thereof.

Suitable winterizing agents include, without limitations, alcohols, glycols, formates, other freezing point depressant, or mixtures or combinations thereof.

Experiments of the Invention

Process Chemistry

Hydrolysis of Nitrilotriacetonitrile

On a commercial scale process, it takes about a couple of days to produce a batch of a hydrolyzed nitrilotriacetonitrile composition. The current process involves adding nitrilotriacetonitrile (NTAN) to a hydrochloric acid (HCl) solution (or other acid solution) over a 12 hour period followed by a 1 hour hold. After the 1 hour reaction hold, the batch is worked up over an additional 10 hour period of time. To gain insight into the chemistry and process step involved in hydrolyzing NTAN, the inventors prepared hydrolyzed NTAN formulations in the laboratory using the current commercial process, modified commercial processes, a prior art (U.S. Pat. No. 3,987,077) process and the new processes of this invention—one bulk NTAN addition, acid or base catalysis, short reaction times, no external heating, and treatment with an oxidizing agent.

One-shot Addition of NTAN

In the novel methods of this invention described herein, a one-shot or bulk addition of NTAN to an acid solution such as a HCl solution was employed. In prior art, the general assumption is that nitrilotriacetonitrile (NTAN) hydrolysis is uncontrollable if NTAN was added over a short period of time, and especially in a one-time addition. To the contrary, no reaction run away was observed when NTAN on 50 g and 100 g scales was added at in one shot to HCl solution. Although reaction temperature reached 90° C. (194° F.) at 1 atmosphere over a 30 minute period of time, but temperature dropped steadily thereafter as shown in FIG. 1. More importantly, the reaction is complete at that point or within a 40 minute period of time. Consequently, NTAN hydrolysis can be efficiently affected in less than 40 minutes via a bulk addition of NTAN to a HCl solution with adequate agitation to permit uniform heating, overhead condensers to condense vaporized solvents, reactants, and/or products and optional cooling to control temperature to prevent potential reaction run away.

One-Shot Addition at $\leq 60°$ C. (140° F.)

Figure 2:
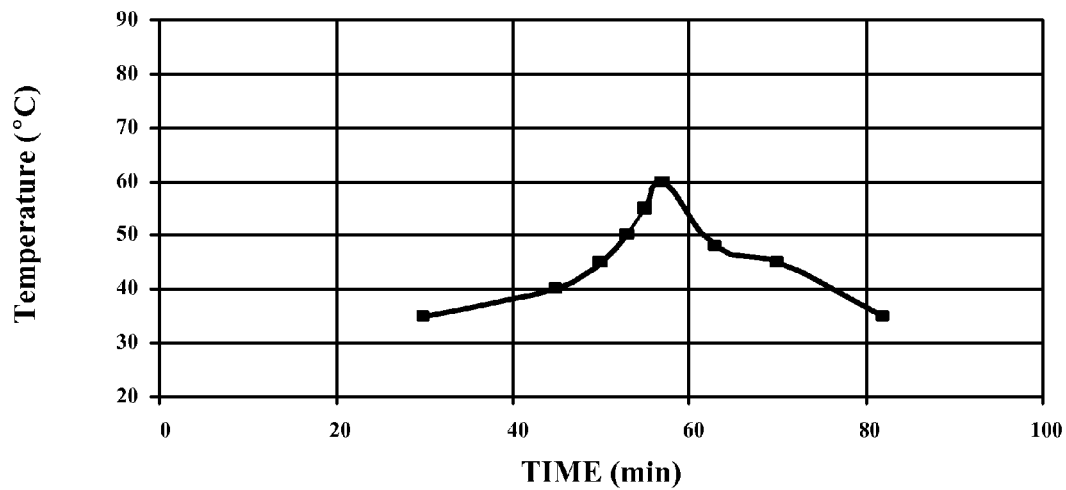
FIG. 2 depicts a reaction profile of NTAN hydrolysis, one-shot addition maintained at 60° C.

Similarly, hydrolyzed NTAN compositions can be prepared by a single NTAN addition, while maintaining the reaction temperature at or below about 60° C. ($\leq 60°$ C. or $\leq 140°$ F.) as shown in FIG. 2. The reaction is complete when the temperature begins to fall, usually within an hour.

Sequential Addition of NTAN over 1 Hour & Treatment at $\leq 60°$ C. (140° F.)

Alternatively, addition of NTAN over 1 hour to a HCl solution and maintaining the reaction temperature at about 60° C. (140° F.) for 3 hours can be used to prepare hydrolyzed NTAN compositions. Here, the protracted addition keeps fresh NTAN in the solution even close to 2 hours into the treatment. Thus, by modifying the current method, complete hydrolysis is achieved in 4 hours total reaction time. In either case, complete hydrolysis must be ascertained by dissolving a sample portion of the reaction solution in aqua ammonia or other basic solution. The reaction is complete if there is no solid suspension seen after addition of base to the reaction sample.

Neutralization Process

The pH of the product is adjusted to a pH between about 7.5 and about 8 with aqua ammonia.

Removal of Residual Cyanide

To remove cyanide concentration to desired low levels or to undetectable levels, the resultant product from hydrolysis and neutralization is treated independently with an oxidizing agent such as sodium chlorite, hypochlorite, ammonium bisulfite, and/or similar oxidizing agents that produce environmentally benign products. The maximum cyanide concentration found in lab or plant samples was less than 60 ppm. Therefore, assuming 60 ppm in the hydrolyzed/neutralized product, a $100^{th}$ concentration (w/w) of hypochlorite or chlorite per Liter to product (3.5 lb of $NaO_2Cl$ or NaOCl per barrel of hydrolyzed/neutralized product) was found to be sufficient to effectively neutralize residual cyanide to an undetectable level.

TABLE 1

Free Cyanide Concentration Before and after Treatment with Sodium Chlorite

| Sample ID | pH | Before Treatment | After Treatment |
| --- | --- | --- | --- |
| 1B1 | 3.36 | 45 ± 5 | 5 ± 5 |
| 1B2 | 7.67 | 45 ± 5 | <1 |
| 5B | 4.26 | 20 ± 5 | 10 ± 5 |
| 5F | 3.18 | 20 ± 5 | <1 |
| 13B | 5.63 | 35 ± 5 | 5 ± 5 |
| 14[1] | 5.24 | <1 | NA |
| 3D | 3.31 | 30 ± 5 | 10 ± 5 (HEAT) |

[1]Reactions that were carried out at high temperatures have undetectable levels of free cyanide.

The required amount of chlorite or hypochlorite was dissolved in calculated amount of deionized water required for normal dilution. Thus, under the basic condition (pH ~8), the product was treated with chlorite/hypochlorite for about 30 minutes at a temperature of about 30° C. (86° F.) with agitation. Then, the pH was adjusted to between 4.5 and 6.0 with HCl.

Physical & Chemical Properties of Constituents

Figure 3A:
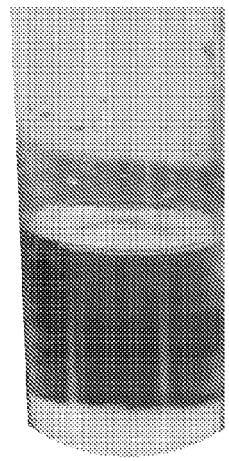
FIG. 3 depicts dissolution of crystals in sample 11A with $NH_4OH$ and products of NTAN hydrolysis
Figure 3B:
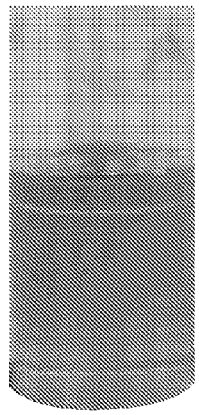
Figure 3C:
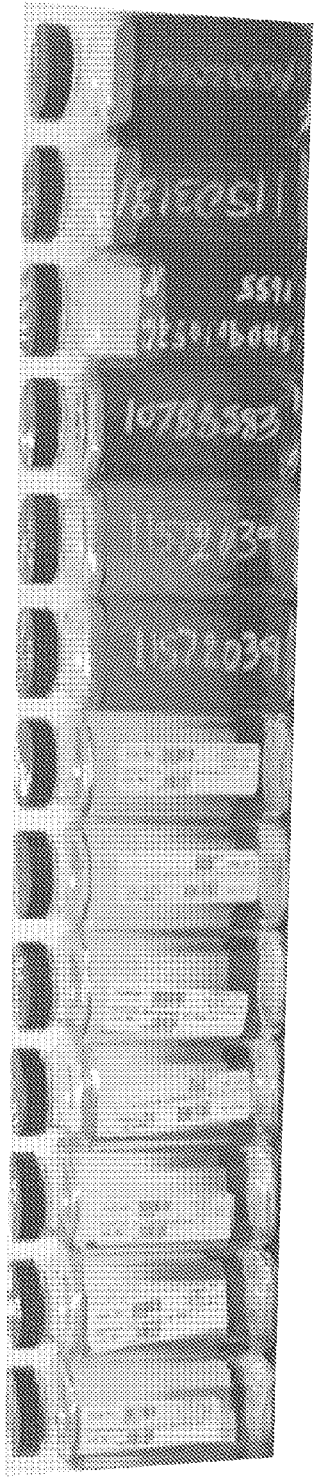

Hydrolyzed NTAN made by existing commercial method is known to form crystals and change color from light yellow to opaque over its shelve life as shown in FIG. 3C.

Crystallization of Hydrolyzed NTAN Components

A neat sample of nitrilotriacetic acid was found to be insoluble in de-ionized water (DI), but soluble in aqua ammonia. In essence, the salt of the acid is soluble whereas the free acid is not soluble in DI. As such, an acidic product can easily form crystals under the right conditions of temperature. Still, when a concentrated solution of the product is formed due to water loss to evaporation or less than required to solubilize the solutes; crystals will form. Therefore, addition of base and/or water is recommended when crystals are observed in transit or storage conditions.

Varied Colors

Figure 4A:
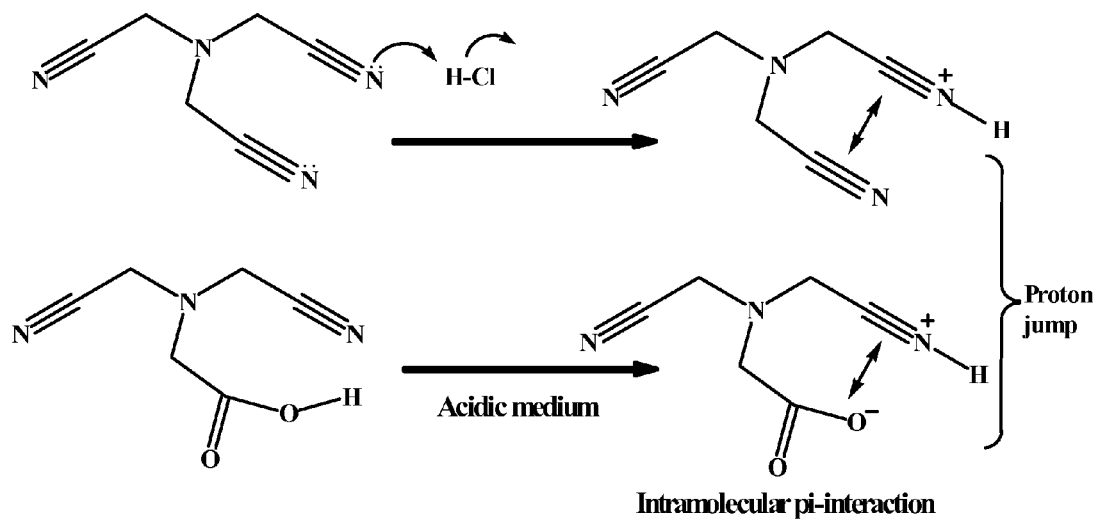
FIG. 4 depicts examples of pi-pi ($\pi$-$\pi$) interactions between components of a hydrolyzed NTAN composition.
Figure 4B:
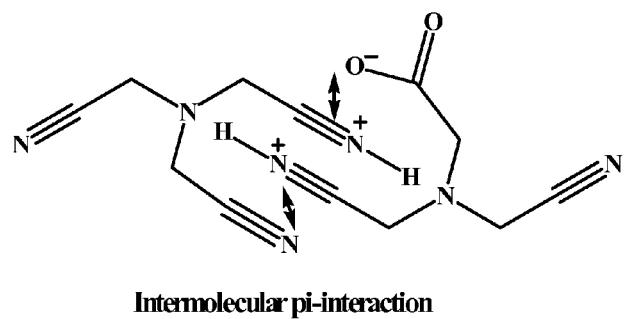

Color is known to accompany $\pi$ to $\pi^*$ transitions that occur in the UV-visible region. Carboxylate, nitrile, amides, amino-acids and other mixtures thereof as shown FIG. 4A are chromophores that can absorb strongly in the UV region with a shoulder in the visible region to produce the light yellow or orange color characteristic of hydrolyzed NTAN. Progressive absorption from 400 nm upwards can eventually lead to the dark color that is often observed. This progression is expected to be catalyzed by protonation and consequent alignment of moieties for it to it interaction as shown in FIG. 4B.

Liquid Chromatography-Mass Spectroscopy (LCMS) Analysis

Figure 5:
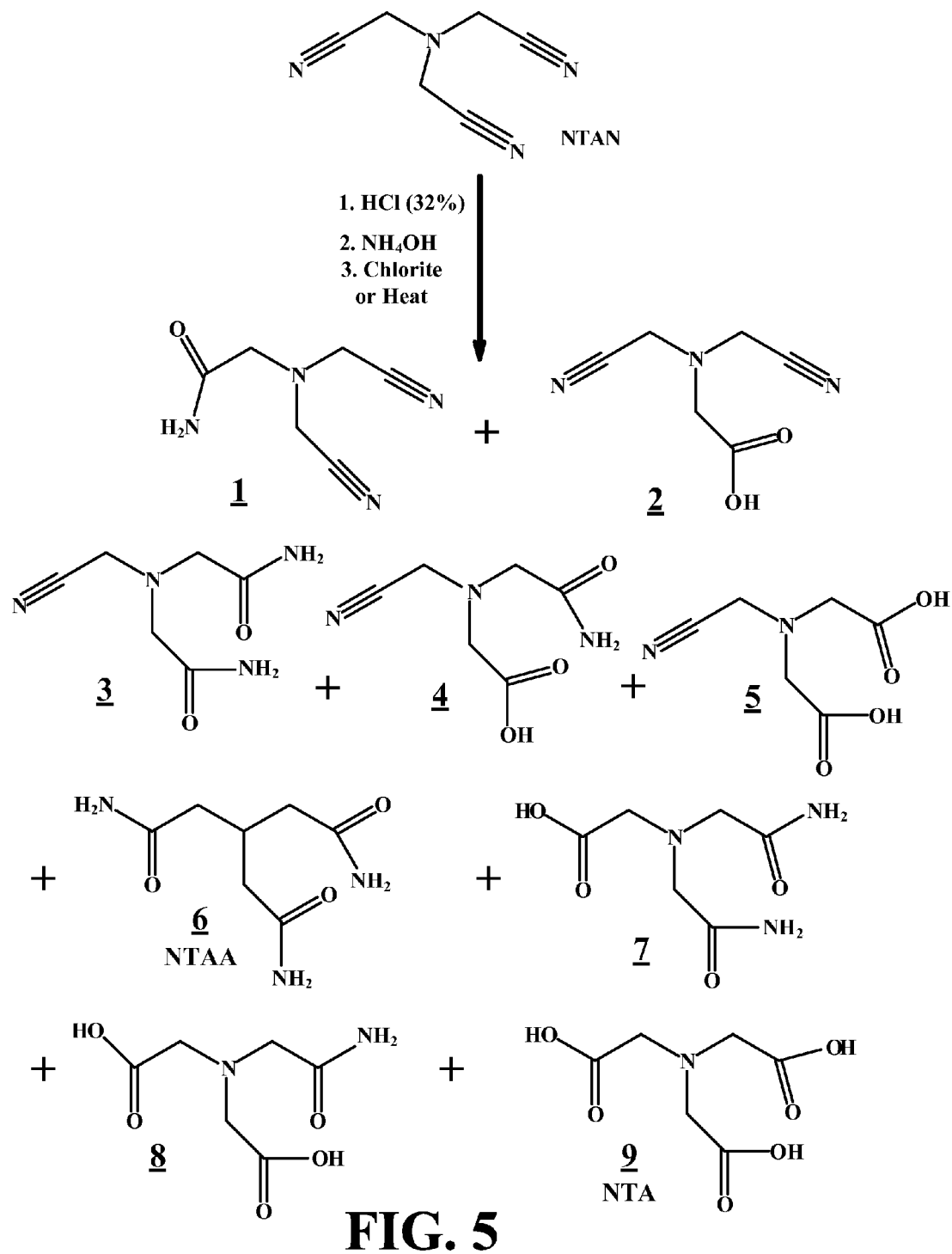
FIG. 5 depicts hydrolysis of nitrilotriacetonitrile.

Liquid Chromatography Mass Spectroscopy (LCMS) analyses were performed on two different hydrolyzed NTAN samples, Lot#0415050 and lot#14879757. LCMS offers advantages of separation of a liquid mixture to pure components and molecular weight determination. Nine distinct adducts are obtainable from the hydrolysis of NTAN as shown in FIG. 5. Despite the fact that components 3, 6 and 8 (Table 2) are predominant in the referenced lots, samples 3 is higher in lot '57; whereas 7 and 8 are higher in lot '50.

TABLE 2

Identified Components of Two Hydrolyzed NTAN Lot Samples Using LCMS

| Comp. | Functional Groups Distribution | Lot# 0415050 (%) | Lot# 14879757 (%) |
|---|---|---|---|
| NTAN | (Acetonitrile)$_3$ | 0.0 | 0.0 |
| 1 | (Acetonitrile)$_2$ (Acetamide) | 0.0 | 0.0 |
| 2 | (Acetonitrile)$_2$ (Acetic acid) | 0.0 | 0.0 |
| 3 | (Acetonitrile) (Acetamide)$_2$ | 34.0 | 46.6 |
| 4 | (Acetonitrile) (Acetamide) (Acetic acid) | 7.4 | 7.2 |
| 5 | (Acetonitrile) (Acetic acid)$_2$ | 0.9 | 0.8 |
| 6 | (Acetamide)$_3$ or NTAA | 34.0 | 31.4 |
| 7 | (Acetamide)$_2$ (Acetic acid) | 19.4 | 12.7 |
| 8 | (Acetamide) (Acetic acid)$_2$ | 3.9 | 1.3 |
| 9 | (Acetic acid)$_3$ or NTA | 0.3 | 0.0 |

Nonetheless, there might be intangible differences in performance. Essentially, analyses of components can be explored to produce most efficient formulation if so desired in the future.

4. FTIR Spectroscopy Analysis

Figure 6:
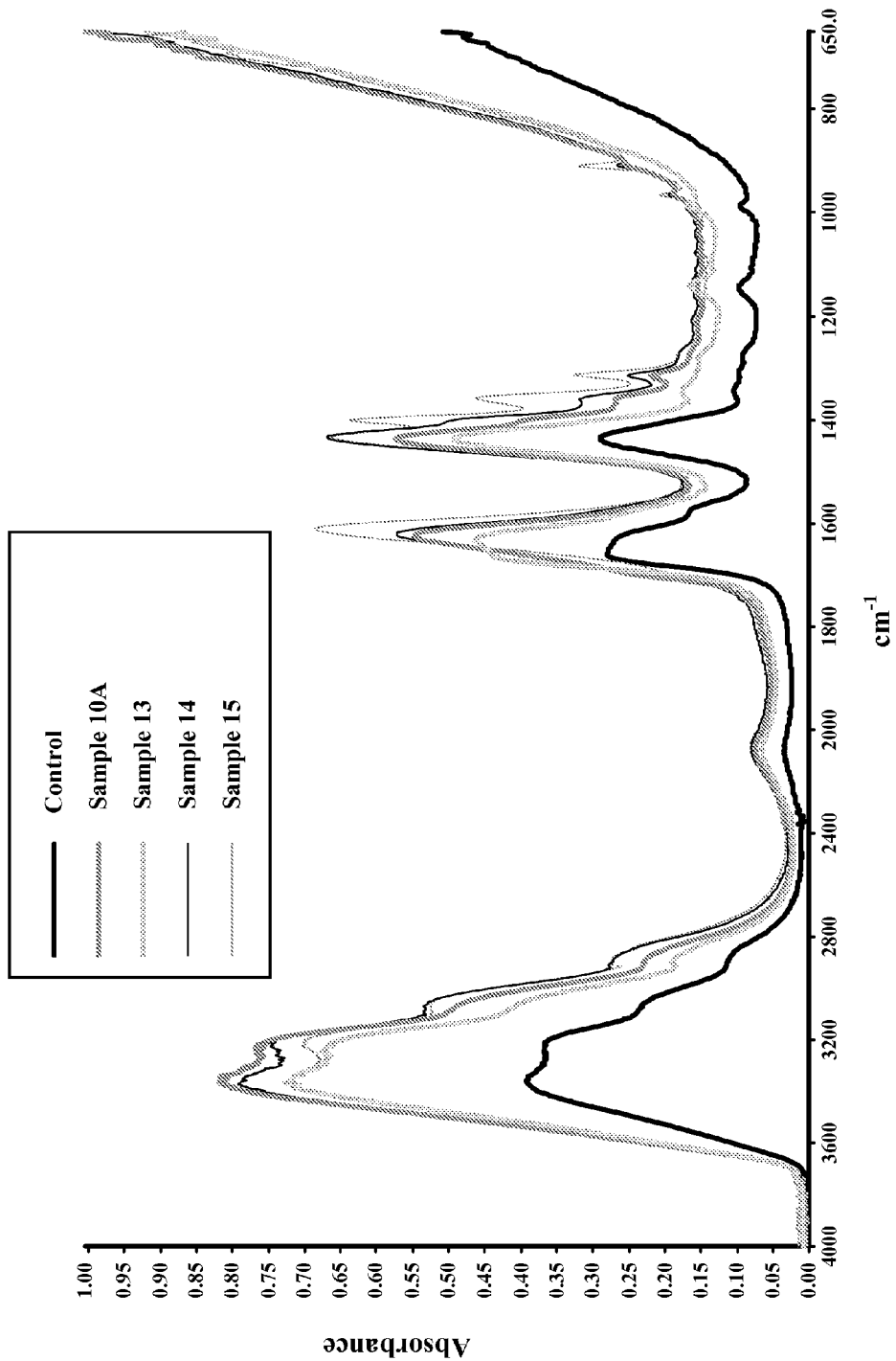
FIG. 6 depicts overlay of FTIR spectra of samples of hydrolyzed NTAN compositions prepared according to different synthetic procedures.
Figure 7:
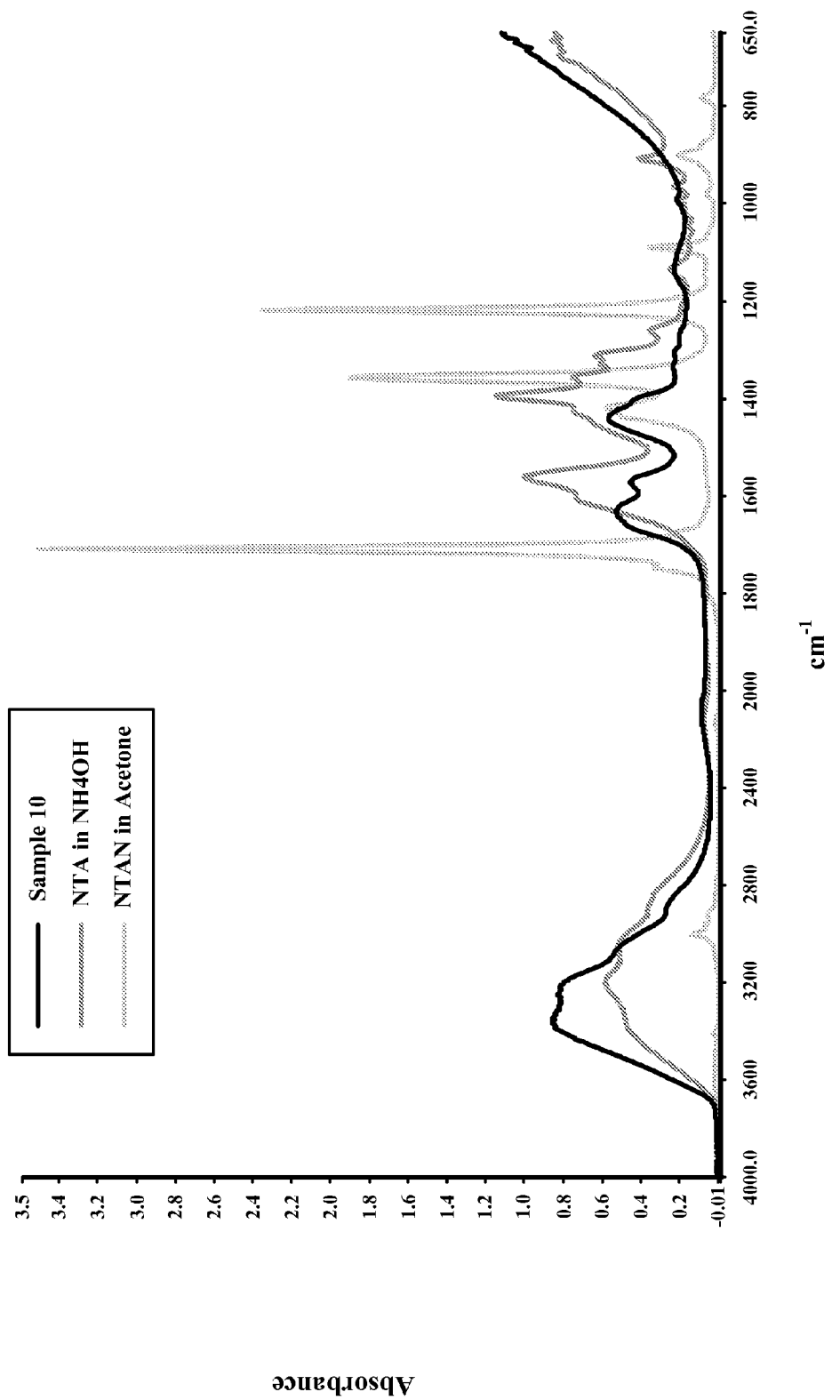
FIG. 7 depicts FTIR spectra of NTAN, NTA solution and sample 10 at pH 9.22.

In the FTIR spectra as shown in FIG. 6 and FIG. 7, absorptions corresponding to carbonyl of amide ($\upsilon_{C=O}$ 1690-1650 cm$^1$) or acid ($\upsilon_{C=O}$ 1660-1550 cm$^1$) moieties, nitrile ($\upsilon^{C=N}$ 3300 cm$^{-1}$ and 1450 cm$^{-1}$), and N—H ($\upsilon_{N=O}$ 3300 cm$^-$ doublet) stretches are present; thus corroborating the LCMS data given above.

Laboratory Synthesis of Hydrolyzed NTAN Compositions

Example 1

Commercial Process

Hydrochloric acid (HCl, 32%, 200 g, 1.56 moles, 20 degree Baume) was placed in a 1,000 mL round bottom reaction flask equipped with a magnetic stirrer, a heating plate, a condenser, and an ice-bath. Nitrilotriacetonitrile (NTAN, 50 g, 0.37 moles), was added over 4 hours in 10% increments while stirring the resulting mixture and maintaining the temperature between 25-60° C. (77-140° F.). Then, the resultant white slurry was stirred for an additional 4 hour to permit complete hydrolysis.

Aqua ammonia (125 g, 29.4%, 26 degree Baume, 1.04 moles) was added to the mixture until a pale yellow color appears (pH=2.77), while maintaining the temperature below 60° C. (140° F.). The solution was diluted with deionized water (115 g, 5.70 moles) and the pH was adjusted to 5 by adding aqua ammonia to give 482.67 g of a product designated sample 3. [Note: The hydrolysis was incomplete because the last portion of NTAN was acid-treated for 1 hour of reaction following the addition of the final shot of NTAN.]

Example 2

One-Shot Addition of NTAN

The same procedure described above was followed, however NTAN was added in one shot to a HCl solution (using same reagent quantities), while stirring the resulting mixture vigorously. The reaction temperature rose gradually from 25° C. to 90° C. (77° F. to 194° F.) in 35 minutes giving a transparent light yellow solution. At about 90° C. (194° F.), the mixture refluxed gently. Solubility test showed complete hydrolysis of NTAN. The temperature then dropped steadily to 140° F. within 5 min. A portion (61.15 g) was withdrawn and treated with aqua ammonia (42.46 g, 26 degree Baume) and diluted with deionized water (20 g, DI) to dissolve suspended solids giving sample 14 (123.61 g, see FIG. 1). The remaining portion of the reaction mixture was refluxed for 1 h at ~98° C. Similar work up produced 385.6 g of a product designated sample 15.

Example 3

One-time Addition of NTAN (Temperature kept under 140° F.)

Following the same procedure described in method A above, and using the same reagent quantities, NTAN was added in one shot to a HCl solution, while stirring the resulting mixture, and maintaining temperature between 25° C. (77° F.) and 60° C. (140° F.). The hydrolysis was complete in one hour.

Aqua ammonia (114 g, 29.4%, 0.9576) was added to the mixture, a pale yellow color appeared, while maintaining the temperature below 60° C. (140° F.). The solution was diluted with DI water (115 g) and the pH was adjusted to 5 by adding aqua ammonia (30 g, 0.86 moles) to give 504 g of a product designated sample 12. [The same procedure was repeated on a 100 g scale. Both temperature and reaction time were found to be the same.]

Example 4

One-Hour Sequential Addition of NTAN

In the same manner described in method A above, NTAN (50 g, 0.37 moles) was added to a HCl solution (200 g of 20 degree Be, 32%) over 1 hour period of time. While stirring the resulting mixture and maintaining the reaction temperature at a temperature≦60° C. (140° F.), the reaction was continued for 3 hours. Following a positive solubility test, aqua ammonia (128 g, 29.4%, 1.05 moles) was added to the mixture (now a pale yellow), while maintaining the temperature below 60° C. (140° F.). The solution was diluted with DI (130 g, pH 9.4) to give 455 g of a product designated sample 5.

Sodium Chlorite & Hypochlorite Treatment

Generally, after adjusting solution pH to between 2-5, the resultant products were treated with sodium hypochlorite or chlorite in a ratio of 1/100 (w/w) for 30 min. After the treatment, free cyanide analyses were carried out as described herein. Products were either completely cyanide free or left with permissible trace levels of cyanide. For effective removal of cyanide in large scale, chlorite is added under basic condition (pH ~8) and the cyanide free product can then be adjusted to a pH between 5 and 6.

Free Cyanide Test Procedure

This test was performed using HACH Cyanide test Kit (Produced by Hach Company, Loveland Colo., USA), Range 0-0.3 mg/L, Model CYN-3 and Cat. No. 2010-02.

The free cyanide test procedure starts by diluting a sample a 1000 times.

If the sample is turbid, the sample is filtered before testing as follow: Place a peace of folded filter paper in a funnel and set it on top of a square mixing bottle. Pour the diluted sample through the filter paper and allow enough to pass through the filter to fill the square bottle to the shoulder.

Use clippers to open one hexaVere™ powder pillow. Add the contents of the pillow to the mixing bottle and swirl to mix.

Add the content of one CyaniVer™ 3 cyanide reagent powder pillow to the mixing bottle, and swirl to mix and allow to stand undisturbed for 1 minute.

Add the content of one CyaniVer™ 4 cyanide reagent powder pillow to the mixing bottle and proceed immediately to the next step.

Add the content of one CyaniVer™ 5 cyanide reagent powder pillow to the bottle, and swirl to mix. If Cyanide is present, a pink color will develop and turn blue in a few minutes. Allow at least 20 minutes, but not more than 26 minutes for full color development.

Fill a color viewing tube to the 5 mL mark with untreated water sample. Place it in the left top opening of comparator.

Hold the comparator up to a light source such as the sky, a window or lamp and view through the openings in front. Rotate the disc to obtain a color match. Read the mg/L cyanide concentration (CN) through the scale window.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A hydrolyzed nitrilotriacetonitrile composition prepared by a process comprising:
    adding an amount of nitrilotriacetonitrile (NTAN) to a solution including an acid catalyst in a single or bulk addition with stirring to form a reaction mixture,
    hydrolyzing the NTAN in the reaction mixture with stirring for a period of time no more than about 1 hour with no external heating to form a hydrolyzed reaction mixture, after hydrolyzing, adjusting the pH of the hydrolyzed reaction mixture to a pH of at least 8 to form a crude hydrolyzed NTAN composition, and
    contacting the crude hydrolyzed NTAN composition with an effective amount of an oxidizing agent for a time and at a temperature sufficient to minimize a concentration of free cyanide in the crude hydrolyzed NTAN composition to a desired low level to form a hydrolyzed NTAN composition having the desired low level of free cyanide.

2. The composition of claim 1, further comprising:
    adjusting the pH of the hydrolyzed NTAN composition to a pH between about 5 and about 7.

3. The composition of claim 1, further comprising:
    concentrating the hydrolyzed NTAN composition to produce a solid product.

4. The composition of claim 1, where the acid catalyst is selected from the group consisting of mineral acids, organic acids and mixtures or combinations thereof.

5. The composition of claim 1, where the acid catalyst is selected from the group consisting of HCl, HBr, sulfuric acid, triflic acid, nitric acid, formic acid, acetic acid, trifluoroacectic acid, trichloroacetic acid, and mixtures or combinations thereof.

6. The composition of claim 1, where the oxidizing agent is selected from the group consisting of alkali hypochlorites, alkali chlorites, alkaline metal hypochlorites, alkaline metal chlorites, alkali bisulfites, alkaline bisulfites, ammonium bisulfite, sulfur dioxide, sulfur trioxide, chlorine, bromine, and mixtures or combinations thereof.

7. The composition of claim 1, where the oxidizing agent is selected from the group consisting of lithium hypochlorite (LiOCl), sodium hypochlorite (NaOCl), potassium hypochlorite (KOCl), cesium hypochlorite (CsOCl), rubidium hypochlorite (RbOCl), lithium chlorite (LiClO$_2$), sodium chlorite (NaClO$_2$), potassium chlorite (KClO$_2$), cesium chlorite (CsClO$_2$), rubidium chlorite (RbClO$_2$), ammonium bisulfite, sulfur dioxide, sulfur trioxide, chlorine, bromine, and mixtures or combinations thereof.

8. The composition of claim 1, further comprising:
    adding an effective amount of a winterizing agent to the hydrolyzed NTAN composition, where the effective amount of the winterizing agent is sufficient to reduce or minimize precipitate formation.

9. The composition of claim 8, where the winterizing agent is selected from the group consisting of alcohols, glycols, formates, other freezing point depressant, or mixtures or combinations thereof.

10. The composition of claim 1, where the cyanide level is below a detectable level.

* * * * *